US012681115B2

(12) United States Patent (10) Patent No.: US 12,681,115 B2
Herrler et al. (45) Date of Patent: Jul. 14, 2026

(54) OPTIMIZING A PULSE SEQUENCE USING AN OPTIMIZATION MAP

(71) Applicant: Siemens Healthineers AG, Forchheim (DE)

(72) Inventors: Jürgen Herrler, Erlangen (DE); Patrick Liebig, Erlangen (DE)

(73) Assignee: SIEMENS HEALTHINEERS AG, Forchheim (DE)

( * ) Notice: Subject to any disclaimer, the term of this patent is extended or adjusted under 35 U.S.C. 154(b) by 0 days.

(21) Appl. No.: 18/824,536

(22) Filed: Sep. 4, 2024

(65) Prior Publication Data

US 2025/0076432 A1 Mar. 6, 2025

(30) Foreign Application Priority Data

Sep. 4, 2023 (DE) ..................... 10 2023 208 496.1

(51) Int. Cl.
G01R 33/44 (2006.01)
A61B 5/055 (2006.01)
G01R 33/28 (2006.01)
G01R 33/54 (2006.01)

(52) U.S. Cl.
CPC ............ G01R 33/443 (2013.01); A61B 5/055 (2013.01); G01R 33/288 (2013.01); G01R 33/543 (2013.01)

(58) Field of Classification Search
CPC .. G01R 33/443; G01R 33/288; G01R 33/543; G01R 33/246; G01R 33/243; G01R 33/5612; A61B 5/055
See application file for complete search history.

(56) References Cited

U.S. PATENT DOCUMENTS

| | | | | |
|---|---|---|---|---|
| 9,606,208 B2 * | 3/2017 | Paul | ................... | G01R 33/5612 |
| 2009/0177075 A1 * | 7/2009 | Derakhshan | ....... | G01R 33/5614 |
| | | | | 600/410 |
| 2010/0121179 A1 * | 5/2010 | Min | ..................... | G01R 33/583 |
| | | | | 600/421 |
| 2010/0127703 A1 * | 5/2010 | Sung | ..................... | A61B 5/055 |
| | | | | 324/309 |
| 2012/0256626 A1 | 10/2012 | Adalsteinsson et al. | | |

(Continued)

OTHER PUBLICATIONS

"Dielectric Artifact—Questions and Answers in MRI" 2010; 20:2-13, https://mri-q.com/dielectric-effect.html). pp. 1-2.

(Continued)

*Primary Examiner* — Baisakhi Roy
(74) *Attorney, Agent, or Firm* — Lempia Summerfield Katz LLC

(57) ABSTRACT

A method for optimizing a pulse sequence includes acquiring a B0 map. A B1 map is acquired for each of at least one transmission channel of a magnetic resonance apparatus. Based on the acquired B0 map and at least one B1 map, a preliminary dynamic pulse is established. For each of the at least one transmission channel, the preliminary dynamic pulse includes a preliminary RF pulse. At least one optimization map is established based on the preliminary dynamic pulse. Each of the at least one optimization map describes a distribution of an optimization parameter resulting from the preliminary dynamic pulse. An initial pulse sequence is provided. An optimized pulse sequence is established based on the initial pulse sequence and the optimization map.

18 Claims, 4 Drawing Sheets

(56) References Cited

U.S. PATENT DOCUMENTS

| | | | |
|---|---|---|---|
| 2012/0268130 A1* | 10/2012 | Fautz | G01R 33/4616 |
| | | | 324/318 |
| 2014/0266195 A1* | 9/2014 | Levin | G01R 33/56509 |
| | | | 324/309 |
| 2015/0293197 A1* | 10/2015 | Taniguchi | G01R 33/543 |
| | | | 324/309 |
| 2017/0168128 A1* | 6/2017 | Feiweier | G01R 33/443 |
| 2019/0162805 A1* | 5/2019 | Wang | G01R 33/543 |
| 2022/0296119 A1* | 9/2022 | Grodzki | A61B 5/1113 |
| 2023/0280428 A1* | 9/2023 | Grodzki | G01R 33/5659 |
| | | | 324/307 |

OTHER PUBLICATIONS

Bloch, Felix. "Nuclear induction." Physical review 70.7-8 (1946): 460-474.

Gras, Vincent, et al. "Universal pulse design of refocusing kT-point pulses using parallel transmission: application to three-dimensional T2-weighted sequences at 7T." (2017).

Herrler, Jürgen, et al. "Fast online-customized (FOCUS) parallel transmission pulses: a combination of universal pulses and individual optimization." Magnetic resonance in medicine 85.6 (2021): 3140-3153.

Hetherington, Hoby P., et al. "Dynamic B0 shimming for multiband imaging using high order spherical harmonic shims." Magnetic resonance in medicine 85.1 (2021): 531-543.

Malik, Shaihan J., et al. "Direct signal control of the steady-state response of 3D-FSE sequences." Magnetic resonance in medicine 73.3 (2015): 951-963.

Pauly, John, et al. "Parameter relations for the Shinnar-Le Roux selective excitation pulse design algorithm (NMR imaging)." IEEE transactions on medical imaging 10.1 (1991): 53-65.

Tomi-Tricot, Raphael, et al. "Fully integrated scanner implementation of direct signal control for 2D T2-weighted TSE at ultra-high field." Proc. Intl. Soc. Magn. Reson. Med. vol. 29. 2021.

Weigel, Matthias. "Extended phase graphs: dephasing, RF pulses, and echoes—pure and simple." Journal of Magnetic Resonance Imaging 41.2 (2015): 266-295.

Yetisir, Filiz, et al. "Parallel transmission 2D RARE imaging at 7T with transmit field inhomogeneity mitigation and local SAR control." Magnetic resonance imaging 93 (2022): 87-96.

* cited by examiner

FIG 1

OPTIMIZING A PULSE SEQUENCE USING AN OPTIMIZATION MAP

This application claims the benefit of German Patent Application No. DE 10 2023 208 496.1, filed on Sep. 4, 2023, which is hereby incorporated by reference in its entirety.

BACKGROUND

The present embodiments relate to optimizing a pulse sequence.

In medical technology, imaging using magnetic resonance (MR), also referred to as magnetic resonance tomography (MRT) or magnetic resonance imaging (MRI), is distinguished by its high soft-tissue contrast levels. Herein, a patient is positioned in a patient receiving region of a magnetic resonance apparatus. During a magnetic resonance scan, radio frequency (RF) transmitting pulses may be radiated into the patient with the aid of one or more transmitting antennae, so that a radio frequency excitation field, the B1 field, is generated. In addition, with the aid of a gradient coil unit of the magnetic resonance apparatus, gradient pulses are output, by which temporary gradient magnetic fields are overlaid onto a static main magnetic field, the B0 field. Via the pulses that are generated, nuclear spins are excited in the patient, and positionally encoded magnetic resonance signals are triggered. The magnetic resonance signals that are triggered are received by the magnetic resonance apparatus and are used for the reconstruction of magnetic resonance mappings.

A certain inhomogeneity of the B1 field and of the B0 field is unavoidable. This is caused, for example, by the individual anatomy of the patient under investigation. The B0 inhomogeneities arise, for example, via the susceptibility of the biological tissue, which has an influence on the static magnetic field. Thus, for example, at tissue boundaries, local deviations from the nominal B0 field arise. In the case of a slice-selective excitation, a gradient magnetic field is applied, and a particular frequency band is selectively excited with an RF pulse. Local B0 field inhomogeneities may disrupt the slice profile in that the slice profile is distorted.

The B1 field inhomogeneities are problematic, or example, in relatively large body parts and at high field strengths, since the wavelength of the radio frequency B1 field decreases in indirect proportion to the increasing B0 field strength. The B1 field inhomogeneities may manifest in signal and contrast variations and even in shadowings in some regions of the resultant magnetic resonance mappings.

In the case of parallel transmission (pTx), the B1 field is generated by the overlaying of a plurality of B1 fields, each of which is generated by a transmission channel. Via an individual control of these transmission channels, the entire generated B1 field may be manipulated in a targeted manner.

In addition to temporally variable B1 fields, dynamic pulses may make use simultaneously of gradient magnetic fields adapted thereto, which may act in a targeted manner upon the precession speed and therefore the dephasing of the excited nuclear spins. The strength of the B1 field and the phase relationship between the B1 field and the momentary phase of the preceding nuclear spin has an influence on how strongly the nuclear spins change their orientation and thus generate the measurable magnetic resonance signal (e.g., transverse magnetization).

The B0 field inhomogeneities arise, for example, via the susceptibility of the biological tissue, which has an influence on the main magnetic field. Thus, for example, at tissue boundaries in the patient, local deviations from the nominal B0 field arise. In the case of a slice-selective excitation, a gradient field is applied, and a particular frequency band is selectively excited with an RF pulse. Local B0 field inhomogeneities therefore disrupt the slice profile, which becomes "curved." For example, a transverse MR slice image of the head of the patient therefore does not necessarily correspond exactly to a transverse cross-section through the scanned head, but rather, further forward in the head (anterior) (e.g., close to the frontal sinus) may represent anatomies further up in the body as further back in the head (posterior).

In addition, due to the RF transmitting pulses, particularly with large field strengths, a large SAR burden on the patient may arise (e.g., when two-dimensional TSE sequences are used). Since the SAR burden at high field strengths typically varies locally, problematic SAR hotspots may possibly occur in the patient. As a result, the resolution and/or duration of the pulse sequence is restricted. Dynamic parallel transmitting pulses also have the potential, in principle, via different B1 fields, of generating different SAR hotspots and so of distributing the local SAR burden better within the patient. In this way, a higher power level in the transmission channels may be enabled without exceeding any SAR limits. As described above, however, such dynamic pTx pulses have previously not been used in two-dimensional TSE sequences.

SUMMARY AND DESCRIPTION

The scope of the present invention is defined solely by the appended claims and is not affected to any degree by the statements within this summary.

The present embodiments may obviate one or more of the drawbacks or limitations in the related art. For example, a pulse sequence that uses dynamic pulses for investigating a patient with a magnetic resonance apparatus is provided. Independent of the grammatical term usage, individuals with male, female, or other gender identities are included within the term.

A computer-implemented method is provided for optimizing a pulse sequence for investigating a patient with a magnetic resonance apparatus. Therein, a B0 map is acquired. In addition, a B1 map is acquired for each of at least one transmission channel of the magnetic resonance apparatus. Based on the acquired field maps (e.g., the B0 map and the at least one B1 map), a preliminary dynamic pulse is established. For each transmission channel of the at least one transmission channel, the preliminary dynamic pulse includes a preliminary RF pulse. At least one optimization map is established based on the preliminary dynamic pulse. Therein, each optimization map of the at least one optimization map describes a distribution of an optimization parameter resulting from the preliminary dynamic pulse. Further, an initial pulse sequence (e.g., to be optimized) is provided. An optimized pulse sequence is established based on the initial pulse sequence and the at least one optimization map.

In one embodiment, magnetic resonance signals are acquired in accordance with the optimized pulse sequence (e.g., in the context of a magnetic resonance investigation, such as a magnetic resonance scan, of the patient). From the magnetic resonance signals, one or more magnetic resonance mappings may be established (e.g., reconstructed). In one embodiment, these magnetic resonance mappings represent mappings of at least a portion of the body of the patient (e.g., a slice of the body of the patient).

In one embodiment, the B0 map describes a B0 field distribution (e.g., spatial distribution) generated by a main magnet of the magnetic resonance apparatus in an investigation region in which, for example, a portion of the patient that is to be investigated is positioned. For example, the B0 map includes a plurality of pixels (e.g., in the case of a two-dimensional B0 map) or voxels (e.g., in the case of a three-dimensional B0 map) and assigns a B0 value (e.g., a (local) strength of the B0 field) to each pixel or voxel of the plurality of pixels or voxels.

The at least one transmission channel for which a B1 map is acquired may be one transmission channel or a plurality of transmission channels that are available to the magnetic resonance apparatus. In one embodiment, B1 maps are acquired only for the transmission channels that are used in a magnetic resonance scan according to the optimized pulse sequence. This may be all the transmission channels available to the magnetic resonance apparatus or just a portion thereof.

In one embodiment, the B1 map describes a B1 field distribution (e.g., spatial distribution) generated by the respective transmission channel of the magnetic resonance apparatus in the investigation region in which, for example, the portion of the patient that is to be investigated is positioned. For example, a respective B1 map includes a plurality of pixels, for example, in the case of a two-dimensional B1 map, or voxels, for example, in the case of a three-dimensional B1 map, and assigns a B1 value (e.g., a (local) strength of the B1 field) to each pixel or voxel of the plurality of pixels or voxels.

In one embodiment, the at least one optimization map describes a distribution (e.g., spatial distribution) of the optimization parameter in the investigation region in which, for example, the portion of the patient that is to be investigated has been positioned. In one embodiment, the optimization parameter describes a property that results when a plurality of pulse sequence pulses of the initial pulse sequence and/or of the optimized pulse sequence are taken into account.

For example, the respective optimization map includes a plurality of pixels, for example, in the case of a two-dimensional optimization map, or voxels, for example, in the case of a three-dimensional optimization map, and assigns a value (e.g., local value) of the optimization parameter to each pixel or voxel of the plurality of pixels or voxels.

The portion of the patient to be investigated may be, for example, a body part or a portion of a body part of the patient (e.g., the head or a portion of the head). The scan region is, for example, the spatial region from which the B0 and B1 maps are acquired. This may be defined in advance, for example, via an operating person of the magnetic resonance apparatus.

A variety of techniques for acquiring B0 and B1 field maps are known. Such techniques are often designated B0 mapping or B1 mapping. The acquisition of the field maps may take place, for example, in a pre-scan before a main scan of a magnetic resonance investigation of the patient. For example, the actual diagnostic magnetic resonance data (e.g., the magnetic resonance signals) are recorded in the main scan. In one embodiment, the main scan may then take place in accordance with the optimized pulse sequence.

A pulse sequence is, for example, a temporal sequence of different sequence modules. Such sequence modules may include, for example, RF pulses (e.g., RF excitation pulses and/or RF refocusing pulses), gradient pulses (e.g., for slice selection, frequency encoding, and/or phase encoding) and/or RF readout modules. There are different types of pulse sequences, such as a TSE sequence, that may differ, for example, in their structure and/or their composition.

A transmission channel may include, for example, a transmitting antenna that is configured to emit an RF pulse. The transmitting antenna may be, for example, part of a radio frequency antenna unit of the magnetic resonance apparatus. For example, the radio frequency antenna unit may include a local coil (e.g., a head coil with one or more transmitting antennae). A local coil may be arranged close to the patient. For example, in the case of magnetic resonance apparatuses with large field strengths (e.g., 7 tesla), a local transmitting coil may be more suitable than a whole body coil fixedly integrated into the magnetic resonance apparatus. Apart from one or more transmitting antennae, the local coil may also have one or more receiving antennae that may be configured to receive magnetic resonance signals.

A transmission channel may also include a unit that transmits a transmission signal (e.g., an electrical transmission signal) to the transmitting antenna. Such a unit may include, for example, an amplifier that is configured to amplify such a transmission signal. A transmission channel may include, for example, a transmission chain with a plurality of components, such as an amplifier, electrical lines, and/or a transmitting antenna.

A dynamic pulse may be a pulse via which a particular flip angle and/or frequency distribution is set in a targeted manner in the image space. For this, the at least one preliminary RF pulse of the preliminary dynamic pulse may have a complex temporal progression. For example, a dynamic pulse includes a multi-channel RF pulse (e.g., a plurality of preliminary RF pulses) that may be transmitted (e.g., simultaneously) using a plurality of transmitting antennae transmitting in parallel.

The establishment of the dynamic pulse, the at least one optimization map, and/or the optimized pulse sequence may take place, for example, with a computation unit of the magnetic resonance apparatus. For example, the computation unit may include one or more processors and/or storage modules (e.g., memory) for carrying out computation operations. The computation unit may be, for example, part of a system control unit of the magnetic resonance apparatus. The provision of the initial pulse sequence may take place, for example, using a provision unit of the magnetic resonance apparatus. For example, the initial pulse sequence is retrieved from a database and/or is parameterized by an input unit of the magnetic resonance apparatus.

In one embodiment, the optimized pulse sequence is established based on the initial pulse sequence and the at least one optimization map via an optimization of the magnetic resonance signal across a plurality of acquired echoes (e.g., their maximization with a weighting of the individual echoes).

In one embodiment, the at least one preliminary RF pulse of the preliminary dynamic pulse may be scaled. The preliminary RF pulse is able to be scaled, for example, if a mean pulse voltage of the preliminary RF pulse is proportional to the resultant mean flip angle and therein the relative spatial distribution of the flip angles and, for example, the phase of the magnetization does not change. For example, the ratio of the flip angle or the phase at one location to the flip angle or the phase at another location is constant.

For example, if $\alpha(r)$ is a complex value consisting of the flip angle amplitude (e.g., magnitude) and the flip angle phase (e.g., phase) at the location r, then for a particular dynamic pulse, it may be provided as a function of the time-dependent pulse voltages $U_c$ (t) on the transmission channels (e.g., transmission voltage) and of the gradient progressions g(t):

$$\alpha(r) = f(U_c(t), g(t))$$

For a scalable pulse, it is the case that a complex scaling factor $b_{coeff}$ that is multiplied evenly with the channel-specific pulse voltages also influences the flip angle distribution as follows:

$$b_{coeff} * \alpha(r) = f(b_{coeff} * U_c(t), g(t))$$

In one embodiment, the establishment of the dynamic pulse takes place while taking account of at least one first boundary condition. The at least one first boundary condition includes a maximum SAR burden on the patient caused when the dynamic pulse is used and/or a maximum transmission voltage to be applied on the transmission channel when the dynamic pulse is used and/or a maximum length of the dynamic pulse. The maximum transmission voltage to be applied to the transmission channel when the dynamic pulse is used may be normalized, for example, to a flip angle that is to be brought about.

By taking account of the maximum SAR burden, the safety of the patient during a magnetic resonance investigation in which the optimized pulse sequence is used may be enhanced. By taking account of the maximum transmission voltage, the efficiency of the magnetic resonance apparatus may be allowed for (e.g., thereby in particular) any hardware limits of the magnetic resonance apparatus that are taken into account so that the optimized pulse sequence may actually also be carried out. By taking account of the maximum length of the dynamic pulse, the associated RF pulse may be scalable and/or a rapid successive recording of echoes may be achieved.

In one embodiment, the preliminary dynamic pulse also includes at least one gradient pulse. In one embodiment, the at least one gradient pulse is applied in parallel (e.g., simultaneously) with the at least one RF pulse of the dynamic pulse. In one embodiment, the at least one gradient pulse is combined with the at least one RF pulse in order to excite a spatially even flip angle pattern.

In one embodiment, the at least one preliminary RF pulse of the preliminary dynamic pulse has a symmetrical form (e.g., temporally), and the at least one gradient pulse of the preliminary dynamic pulse has a temporally antisymmetrical form. In one embodiment, such forms are particularly well suited to non-selective excitation (e.g., for use in 3D sequences).

In one embodiment, the at least one preliminary RF pulse of the preliminary dynamic pulse has an antisymmetrical form (e.g., temporally), and the at least one gradient pulse of the preliminary dynamic pulse has a temporally symmetrical form (e.g., a conventional slice selection gradient). In one embodiment, such forms are particularly well suited for excitation of a plurality of slices (e.g., for use in SMS sequences).

In one embodiment, the initial and/or optimized pulse sequence is a pulse sequence according to which at least one spin echo and/or at least a stimulated echo is generated. This may be, for example, a Turbo-Spin-Echo (TSE) sequence (sometimes also referred to as Fast-Spin Echo (FSE)) and/or a Sampling Perfection with Application optimized Contrast using different flip angle Evolution (SPACE) sequence and/or a Steady-State Free Precession (SSFP) sequence.

A spin echo may be understood, for example, as the recurrence of a magnetic resonance signal after the decay of an FID signal. For this purpose, for example, a dephasing of the spin (e.g., decay of the transverse magnetization) may be reversed by radiating in a refocusing pulse. The spins return into phase and the spin echo occurs at the time point TE (e.g., the echo time). The FID signal is induced, for example, by an RF excitation of the nuclear spin and, without external influences, decays (e.g., freely) exponentially with a characteristic time constant T2*. Therein, not all the components of the spin are refocused. For example, in the case of a refocusing pulse of less than 180°, a portion of the magnetization may be refocused, for example, after one or more further refocusing pulses and may thus generate a signal (e.g., a stimulated echo).

In one embodiment, the optimized pulse sequence includes at least one optimized dynamic pulse. In one embodiment, the at least one optimized dynamic pulse is derived from the preliminary dynamic pulse. In one embodiment, the derivation of the at least one optimized dynamic pulse from the preliminary dynamic pulse includes a simple multiplication of at least one optimization factor established based on at least one optimization map with the preliminary dynamic pulse.

In one embodiment, the optimization of the initial pulse sequence may be carried out better based on the at least one optimization map than based on the acquired B0 map and/or the acquired B1 maps. In one embodiment, in the optimization of the initial pulse sequence, a dynamic development of the optimization parameter dependent upon the temporal sequence of the initial pulse sequence is taken into account.

In one embodiment, the at least one optimization map includes a flip angle map with a flip angle as the optimization parameter. In one embodiment, the flip angle map includes a complex-valued flip angle map that includes, for example, a flip angle amplitude distribution and a flip angle phase distribution. In one embodiment, the flip angle includes as the optimization parameter a real flip angle amplitude and an imaginary flip angle phase.

An excitation angle, for example, is designated the flip angle for the pulse sequence. Such an excitation angle is, for example, the angle relative to the direction of the main magnetic field by which a net magnetization is rotated by applying an RF pulse at the Larmor frequency.

In one embodiment, the flip angle map describes a distribution (e.g., spatial distribution) of the flip angle in the scan region (e.g., in the investigation region in which the portion of the patient that is to be investigated has been positioned). For example, the flip angle map includes a plurality of pixels, for example, in the case of a two-dimensional flip angle map, or voxels, for example, in the case of a three-dimensional flip angle map, and assigns a flip angle (e.g., a real flip angle amplitude and an imaginary flip angle phase) to each pixel or voxel of the plurality of pixels or voxels.

The flip angle map may be better suited to the optimization of the initial pulse sequence than, for example, the acquired B0 and B1 maps.

In one embodiment, the preliminary dynamic pulse is established under the boundary condition that the resultant flip angle map has the greatest possible homogeneity and/or for selective pulses, also a more exact profile of the slice or slices to be excited. A "bending" of the slice profile by B0 inhomogeneities may thus also be counteracted.

In one embodiment, the flip angle map is established by a Bloch simulation based on the dynamic pulse. For example, for the preliminary dynamic pulse, a Bloch simulation is carried out. The principles of a possible Bloch simulation are set out, for example, in the document by F. Bloch: Nuclear induction. Phys Rev 1946; 70:460-74.

In one embodiment, a flip angle map relating to a nominal (e.g., in principle, arbitrary) flip angle results therefrom. This flip angle map may then be normalized and regarded as a pseudo-B1 map in relation to a maximum voltage value. In one embodiment, such a pseudo-B1 map may be used like a B1 map (e.g., conventional B1 map) in a known method such as, for example, the DISCOVER algorithm in order to calculate, for example, optimization factors (e.g., pseudo-shim factors). Such a calculation may be carried out, for example, for each individual pulse of the initial pulse sequence (e.g., the excitation pulse and the refocusing pulses of a TSE sequence).

In one embodiment, the at least one optimization map includes an SAR map with a specific absorption rate (SAR) as the optimization parameter.

The specific absorption rate describes, for example, a radio frequency energy absorbed per unit time and per kilogram of body weight following RF irradiation. The absorption of the RF energy may lead to heating of the body tissue of the patient. The energy absorption may be an important variable for the ascertainment of safety limit values. Given an inadmissibly high local concentration of RF energy, RF burns may occur (e.g., local SAR). Given even distribution of the RF energy over the entire body, the load on the thermoregulation or the cardiovascular system of the patient is significant (e.g., whole body SAR).

In one embodiment, the SAR map is established by virtual observation points (VOPs) based on the dynamic pulse. Therein, the VOPs represent, for example, coil-specific parameters. In one embodiment, in order to establish the SAR map, an SAR simulation is carried out for the preliminary dynamic pulse based on the virtual observation points. In one embodiment, the SAR map is based on the $[N_{channels}, N_{channels}]$ large VOP matrices (Z) and the voltage progressions of the preliminary dynamic pulse normalized to a flip angle. These RF pulse forms may be represented as $[N_{samples}$ (a sample corresponds to a period with a respective constant voltage), $N_{channels}]$ large matrices (B) and multiplied, as follows, to an exemplary VOP matrix in order to obtain a new value of a pseudo-VOP ($Z_{new}$):

$$Z_{new} = \left( |B^H B \circ Z|_1 \right)$$

In one embodiment, the operator $\circ$ describes the Hadamard product, $B^H$ describes the adjugate of the matrix B, and $\| \ldots \|_1$ describes the sum norm of a matrix. $Z_{new}$ is therefore a number per VOP. Since a plurality of VOP matrices are used for the original SAR monitoring, the SAR map consists of just as many pseudo-VOPs.

In one embodiment, the SAR burden of the preliminary dynamic pulse results therefrom (e.g., relative to a normalized voltage). These may be regarded as pseudo-VOPs (e.g., as the SAR burden per volt).

In one embodiment, when optimization factors are established, the SAR simulation for the VOPs may be used as pseudo-VOPs in order, for example, to calculate an SAR burden of the entire initial pulse sequence and to limit the SAR burden during the optimization.

The concept of the VOPs is described, for example, in the publication US 2012/0256626 A1, and reference is made thereto for further details. For example, the VOPs technique describes a model compression technique in order to determine the voxels with the maximum local SAR (e.g., the hot-spot-candidates) in order to reduce the complexity of the prediction of the local SAR calculations. The VOPs technique allocates, for example, each voxel of a patient-specific model based on the absorption-sensitivity of each voxel, as shown via a pre-calculated spatial matrix S for the model, in clusters. The VOPs technique determines a matrix Aj for each cluster j, where each matrix Aj may be regarded as a virtual observation point that represents all the voxels in the cluster. This set of virtual observation points may be used to predict and control the maximum local SAR, although the set is very small in relation to the total number of voxels in the cluster model.

In one embodiment, in order to establish the optimized pulse sequence, at least one, for example, complex-valued optimization factor is established based on the at least one optimization map. Further, an optimized RF pulse is established for the at least one transmission channel based on the at least one optimization factor and the at least one preliminary RF pulse of the preliminary dynamic pulse. In one embodiment, the established at least one RF pulse is part of the optimized pulse sequence.

In one embodiment, this takes place simply via a multiplication of the at least one optimization factor with the at least one preliminary RF pulse. Since a multiplication is typically particularly simple to perform, the optimized pulse sequence may thus be established particularly easily.

In one embodiment, the initial pulse sequence includes a plurality of, temporally sequential, pulse sequence pulses. A pulse sequence pulse has, for example, an RF pulse (e.g., per transmission channel), and optionally also a gradient pulse (e.g., per gradient coil). In one embodiment, an optimization factor is established for each of the pulse sequence pulses, where for each of the pulse sequence pulses per transmission channel, an optimized RF pulse is established based on the respective optimization factor and the respective preliminary RF pulse.

For example, the initial pulse sequence includes a number N (N>1) of pulse sequence pulses; the dynamic pulse further includes M (M≥1) preliminary RF pulses (e.g., for M transmission channels); for each of the N pulse sequence pulses, an optimization factor is established, and therefore in total, N optimization factors are established. In order to obtain the first of N optimized dynamic pulses, the first of the N optimization factors is multiplied in each case with the M preliminary RF pulses, so that for the first optimized dynamic pulse, M optimized RF pulses are obtained; in order to obtain the second of N optimized dynamic pulses, the second of the N optimization factors is multiplied with the M preliminary RF pulses, so that for the second optimized dynamic pulse, again, M optimized RF pulses are obtained, etc.

In one embodiment, the at least one preliminary RF pulse is scaled with the optimization factors in order to obtain the optimal RF pulse. A scaling of this type may be carried out particularly rapidly.

In one embodiment, the establishment of the optimized pulse sequence (e.g., the at least one optimization factor) takes place using an EPG model and/or in accordance with a DISCOVER method.

Herein, EPG stands for "extended phase graphs". In one embodiment, with the EPG model, the optimization may take place such that thereby, for example, the magnetic resonance signal (e.g., the spatially-resolved magnetic reso-
nance signal) in general (e.g., the magnetic resonance signal
of a particular tissue type or the contrast between two tissue
types) is maximized. For further details of the EPG model,
reference is made to the publication by Matthias Weigel:
Extended phase graphs: dephasing, RF pulses and echoes-
pure and simple. J Magn Reson Imaging. 2015 February; 41
(2): 266-95.

DISCOVER stands herein for "Direct Signal Control with
Variable Excitation and Refocusing Pulses." In the prior art,
however, this method is not applied to optimization maps,
but rather to B1 maps. According to the DiSCoVER method,
for example, a TSE signal model is used in order to modify
relative amplitudes and/or phases in each transmission chan-
nel during a TSE echo train in order to generate a homo-
geneous signal. For example, therein, a specific B1 shim is
calculated for the excitation pulse and each refocusing pulse.
The local B1 field distribution thus changes from pulse
sequence pulse to pulse sequence pulse. These B1 shims
and, with them, also the actual flip angles may be optimized
with the aid of the EPG signal model (as described above).

In one embodiment, the optimization (e.g., the establish-
ing of the at least one optimization factor) takes place while
taking account of a plurality of pulse sequence pulses (e.g.,
all of the pulse sequence pulses of an echo train, over the
excitation pulses and all the refocusing pulses in a TSE/
SPACE/SSFP echo train) of the initial pulse sequence.

For example, this takes place similarly to the DISCOVER
method. As distinct therefrom, in place of the B1 maps, for
example, at least one optimization map (e.g., normalized flip
angle maps) and therefore at least one pseudo-B1 map are
now used in order, for example, for each pulse sequence
pulse (e.g., each excitation and refocusing pulse) to calculate
an optimization factor (e.g., complex optimization factor;
"pseudo-shim factor"). Further, the SAR simulation for the
VOPs may be used as pseudo-VOPs in order to calculate the
SAR burden of the entire pulse sequence and to limit the
SAR burden during the optimization. In one embodiment,
RF pulses (e.g., the pulse shapes) of the preliminary
dynamic pulse are simply multiplied with the optimization
factors. In one embodiment, the optimization factors (e.g.,
similarly to the DiSCoVER method) are optimized such that
the signal shape corresponds to a particular temporal
sequence (e.g., a maximum signal for certain tissue types).

The EPG signal model may be used similarly. Possible
boundary conditions in this optimization that provide a
certain maximum SAR burden (e.g., pseudo-VOPs) and a
component protection (e.g., maximum voltage of the
dynamic pulse results in a maximum flip angle of the pulse
sequence) are adapted accordingly for this optimization.

Further, a magnetic resonance apparatus that is configured
to carry out a method as described above is provided.

The advantages of the magnetic resonance apparatus of
the present embodiments substantially correspond to the
advantages of the method of the present embodiments for
optimizing a pulse sequence for investigating a patient with
the magnetic resonance apparatus, as described in detail
above. Features, advantages, or alternative embodiments
mentioned herein may also be transferred similarly to the
other claimed subject matter and vice versa.

Further, a computer program product that includes a
program and is directly loadable into a memory store of a
programmable system control unit of a magnetic resonance
apparatus, and includes program means (e.g., libraries and
auxiliary functions) in order to carry out a method of the
present embodiments when the computer program product is
executed in the system control unit of the magnetic resonance apparatus is provided. The computer program product
may therein include an item of software with a source code
that is still to be compiled and linked or is only to be
interpreted, or an executable software code that, for execu-
tion, is only to be loaded into the system control unit.

Via the computer program product, the method of the
present embodiments may be carried out rapidly, exactly
reproducibly, and robustly. The computer program product
may be configured so that the computer program product
may carry out the method acts of the present embodiments
by the system control unit. In each case, the system control
unit therein has the pre-conditions such as, for example, a
suitable working memory store, a suitable graphics card, or
a suitable logic unit so that the respective method acts may
be carried out efficiently.

The computer program product is stored, for example, on
a computer-readable medium (e.g., a non-transitory com-
puter-readable storage medium) or is deposited on a network
or server from where the computer program product may be
loaded into the processor of a local system control unit that
may be directly connected to the magnetic resonance appa-
ratus or may be configured as part of the magnetic resonance
apparatus. Further, control information of the computer
program product may be stored on an electronically readable
data carrier. The items of control information of the elec-
tronically readable data carrier may be configured such that
the items of control information carry out a method of the
present embodiments when the data carrier is used in a
system control unit of a magnetic resonance apparatus.

Examples of electronically readable data carriers are a
DVD, a magnetic tape, or a USB stick, on which electroni-
cally readable control information (e.g., software) is stored.
If this control information is read from the data carrier and
stored in a system control unit of the magnetic resonance
apparatus, all the proposed embodiments of the above-
described methods may be carried out.

Further advantages, features, and details are disclosed in
the description below with reference to example embodi-
ments and drawings. Parts that correspond to one another are
provided with the same reference signs in all the drawings.

BRIEF DESCRIPTION OF THE DRAWINGS

FIG. 1 shows a magnetic resonance apparatus with which
a method for optimizing a pulse sequence for investigating
a patient with a magnetic resonance apparatus may be
carried out;

DETAILED DESCRIPTION

Figure 1:
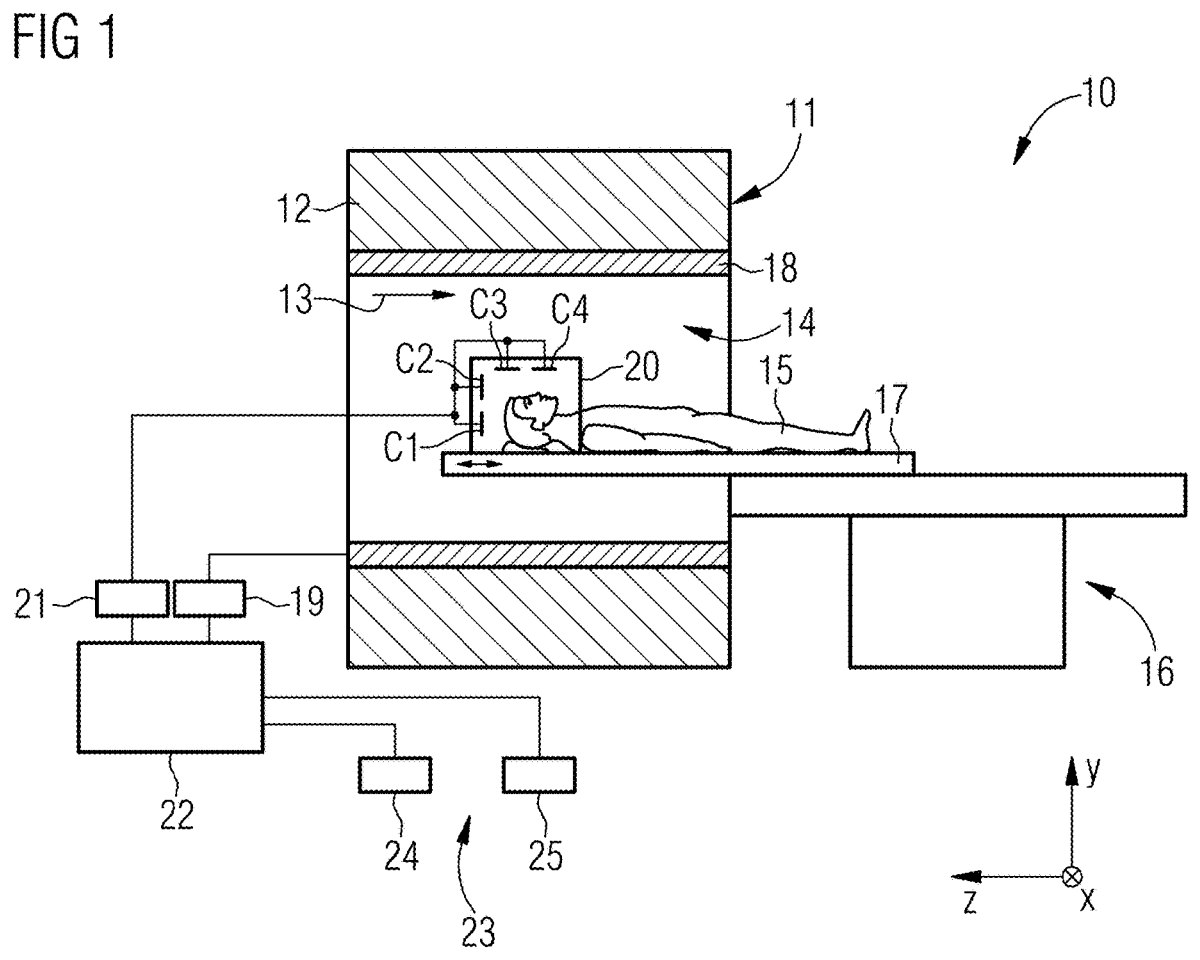
Figure 2:
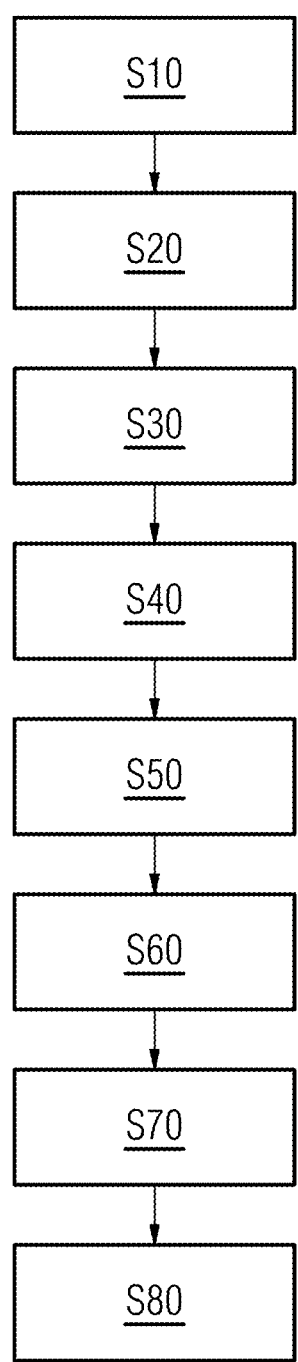
FIG. 2 shows a flow of a method for optimizing a pulse
sequence for investigating a patient with a magnetic reso-
nance apparatus.

Shown schematically in FIG. 1 is a magnetic resonance
apparatus 10 that is configured to carry out a method for
optimizing a pulse sequence. The magnetic resonance appa-
ratus 10 includes a magnet unit 11 that has a main magnet
12 for generating a strong and, for example, temporally
constant main magnetic field 13. In addition, the magnetic
resonance apparatus 10 includes a patient receiving region
14 for accommodating a patient 15. In the present example
embodiment, the patient receiving region 14 is configured cylindrical and is surrounded cylindrically in a circumferential direction by the magnet unit 11. In principle, however, an embodiment of the patient receiving region 14 deviating therefrom may be provided. The patient 15 may be moved by a patient positioning apparatus 16 of the magnetic resonance apparatus 10 into the patient receiving region 14. For this purpose, the patient positioning apparatus 16 has a patient table 17 that is able to be moved within the patient receiving region 14.

The magnet unit 11 also has a gradient coil unit 18 for generating gradient magnetic fields that are used for spatial encoding during an imaging process. The gradient coil unit 18 may include gradient coils (not shown in detail here). For example, the gradient coil unit 18 may include a gradient coil for generating a gradient magnetic field in the x-direction, a gradient coil for generating a gradient magnetic field in the y-direction, and a gradient coil for generating a gradient magnetic field in the z-direction. Using the gradient coils, gradient pulses may be applied for generating the gradient magnetic field. The gradient coil unit 18 is controlled by a gradient control unit 19 of the magnetic resonance apparatus 10.

The magnet unit 11 further includes a radio frequency antenna unit 20 that is configured in the present example embodiment as a local coil. The local coil herein has, by way of example, four transmitting antennae. Each of the transmitting antennae is associated with a transmission channel C1, C2, C3, C4. A multi-channel system of this type may be capable of applying pTx pulses. The radio frequency antenna unit 20 is controlled by a radio frequency antenna control unit 21 of the magnetic resonance apparatus 10 and radiates RF pulses into an examination space that is substantially formed by a patient receiving region 14 of the magnetic resonance apparatus 10. By this, an excitation of atomic nuclei by the main magnetic field 13 generated by the main magnet 12 takes place. Through relaxation of the excited atomic nuclei, magnetic resonance signals are generated. The radio frequency antenna unit 20 may have one or more receiving antennae (not shown here) configured for receiving the magnetic resonance signals. In one embodiment, the magnetic resonance apparatus 10 may include a radio frequency antenna unit 20 in the form of a whole body coil fixedly integrated into the magnetic resonance apparatus 10.

For controlling the main magnet 12, the gradient control unit 19, and for controlling the radio frequency antenna control unit 21, the magnetic resonance apparatus 10 has a system control unit 22. The system control unit 22 centrally controls the magnetic resonance apparatus 10 (e.g., the execution of a pulse sequence, such as an optimized pulse sequence established according to a method for optimizing a pulse sequence for investigating the patient 15). In addition, the system control unit 22 includes an evaluation unit (not shown in detail) for evaluating the magnetic resonance signals that are acquired during the magnetic resonance investigation.

Further, the magnetic resonance apparatus 10 includes a user interface 23 that is connected to the system control unit 22. Control information such as, for example, imaging parameters and reconstructed magnetic resonance mappings may be displayed on a display unit 24 (e.g., on at least one monitor) of the user interface 23 for medical operating personnel. Further, the user interface 23 has an input unit 25 by which information and/or parameters may be input by the medical operating personnel during a scanning procedure.

Figure 3:
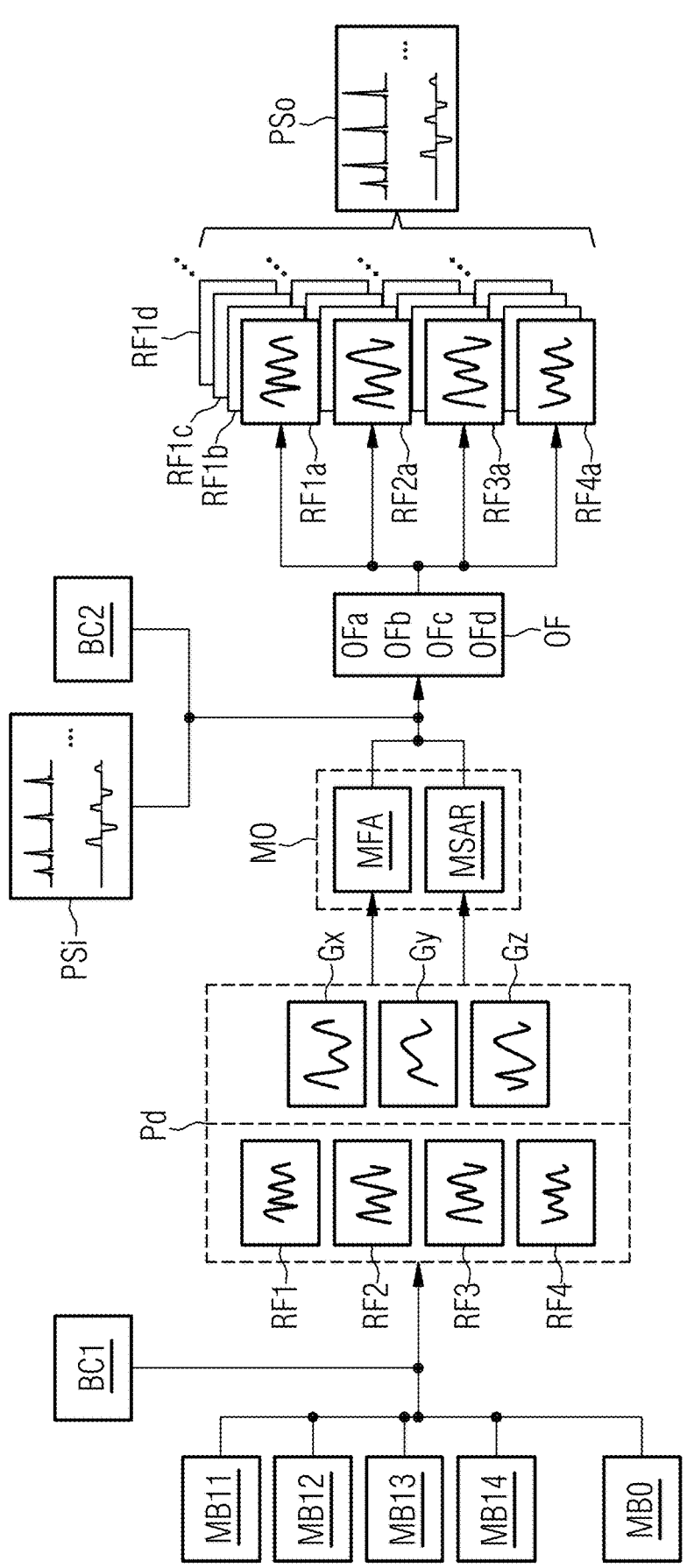
FIG. 3 shows an illustration of a possible method.

Shown schematically in FIG. 2 in conjunction with FIG. 3 is a method for optimizing a pulse sequence for investigating the patient 15 with the magnetic resonance apparatus 10. In S10, a B0 map MB0 and a B1 map MB11, MB12, MB13, MB14 for each of the four transmission channels C1, C2, C3, C4, for example, of the magnetic resonance apparatus 10 are acquired. This acquisition may take place, for example, while the patient 15 is lying in the magnetic resonance apparatus 10. The field maps may serve as the foundation of the optimization.

In S20, at least one first boundary condition BC1 is provided. The at least one first boundary condition BC1 results, for example, from an SAR burden that is to be adhered to, a maximum voltage on the transmission channels, and a maximum pulse length (e.g., with regard to B0 field inhomogeneities and T2*) of the pulses for any given flip angles. In one embodiment, dynamic pulses with symmetrical RF pulses are able to the scaled paired with antisymmetrical gradient pulses and are suitable as nonselective pulses (e.g., 3D sequences). In one embodiment, dynamic pulses with symmetrical gradient pulses (e.g., a conventional slice selection gradient) are able to be scaled paired with antisymmetrical RF pulses and are suitable as multislice-selective pulses (SMS sequences). These symmetry conditions have proved to be adequate with sufficiently short pulses (e.g., 1 to 2 ms) and flip angle variations from 40° to 145° and 100 refocusing pulses following an excitation.

In S30, a preliminary dynamic pulse Pd is established based on the B0 map, the four B1 maps MB11, MB12, MB13, MB14, and the at least one first boundary condition BC1. The preliminary dynamic pulse Pd in this case includes four preliminary RF pulses RF1, RF2, RF3, RF4 and three gradient pulses Gx, Gy, Gz. Therein, each of the four preliminary RF pulses RF1, RF2, RF3, RF4 is associated with one of the four transmission channels C1, C2, C3, C4 (e.g., the preliminary RF pulse RF1 with the transmission channel C1, the preliminary RF pulse RF2 with the transmission channel C2, etc.). Further, each of the three gradient pulses Gx, Gy, Gz is associated with one of the three gradient coils. In accordance with the nature of a dynamic pulse (e.g., a pTx pulse), it is provided that the RF pulses and the gradient pulses may be applied in parallel (e.g., simultaneously) in order to achieve a particular goal. Such a goal may be, for example, a homogeneous nuclear spin excitation.

In S40, two optimization maps MO (e.g., a flip angle map MFA and an SAR map MSAR) are established. The flip angle map MFA describes a distribution of a flip angle resulting from the preliminary dynamic pulse Pd and may be established by a Bloch simulation based on the preliminary dynamic pulse Pd. The flip angle map MFA may relate to a nominal (e.g., arbitrary) flip angle. This flip angle map MFA may then be normalized (e.g., relative to a maximum voltage value of 1 volt) and regarded as a pseudo-B1 map.

The SAR map MSAR describes a distribution of a specific absorption rate resulting from the preliminary dynamic pulse Pd and may be established based on the preliminary dynamic pulse Pd using virtual observation points that are provided. For example (e.g., similarly to the Bloch simulation), an SAR simulation with virtual observation points (VOPs) may be carried out for the pulse provided, from which the SAR burden of the pulse in relation to the normalized voltage is found (e.g., related to a maximum voltage value of 1 volt). The VOPs may herein be regarded as pseudo-VOPs.

In S50, an initial pulse sequence PSi is provided. Herein, four temporally sequential pulse sequence pulses a, b, c, d are implied. A pulse sequence (e.g., the initial pulse sequence PSi) may naturally further include significantly more pulse sequence pulses. The pulse a is, for example, an excitation pulse of a TSE sequence. The pulses b, c, d are, for example, refocusing pulses of the TSE sequence. A pulse sequence pulse may, for example, be a dynamic pulse that includes, for example, a plurality of transmission channel-specific RF pulses and a plurality of gradient coil-specific gradient pulses.

In S60, at least one second boundary condition BC2 is provided. Based on the initial pulse sequence PSi and the at least one second boundary condition BC2, as well as the optimization map MO, in S70, optimization factors OFa, OFb, OFc, OFd are established. In one embodiment, the optimization factors OFa, OFb, OFc, OFd are determined such that thereby a resultant magnetic resonance signal is optimized across a plurality of pulse sequence pulses of the initial pulse sequence PSi. In one embodiment, therein, a possible amendment of a local B1 field distribution from pulse sequence pulse to pulse sequence pulse is taken into account.

The relationship between the B1 field or the RF pulse and the transverse magnetization generated is typically non-linear. Particularly, in the case of TSE sequences, this non-linearity is important to take into account, since many RF pulses with variable, and at times very large, flip angles are used. Shadowings by B1 field inhomogeneities are often clearer in TSE sequences, since each echo depends not only upon the directly preceding refocusing pulse (and its resultant field inhomogeneities), but also upon all the excitation and refocusing pulses therebefore.

In one embodiment, during the optimization, an EPG signal model is used, so that for example, the magnetic resonance signal (e.g., spatially resolved magnetic resonance signal) in general and/or the magnetic resonance signal of a particular tissue type and/or a contrast between two tissue types of the patient 15 is maximized. The fundamental form of the RF pulse RF1, RF2, RF3, RF3 of a transmission channel may not change, but is merely scaled for each pulse sequence pulse of the optimized pulse sequence SPo by the optimization factors OFa, OFb, OFc, OFd. For such a scaling to be possible, it is already taken into account in S30 that the preliminary RF pulses RF1, RF2, RF3, RF4 of the preliminary dynamic pulse Pd are able to be scaled. For example, this may be provided by the previously described symmetry conditions that are provided as the first boundary conditions BC1 in S20.

Each of the optimization factors OFa, OFb, OFc, OFd is therein associated with one of the successive pulse sequence pulses a, b, c, d of the initial pulse sequence PSi. In S80, making use of the optimization factors OFa, OFb, OFc, OFd and the RF pulses RF1, RF2, RF3, RF3 of the preliminary dynamic pulse Pd, RF pulses of optimized dynamic pulses are generated. Therein, for example, based on the optimization factor OFa associated with the pulse sequence pulse a and the RF pulses RF1, RF2, RF3, RF4 of the preliminary dynamic pulse Pd, RF pulses RF1a, RF2a, RF3a, RF4a of an optimized dynamic pulse associated with the pulse sequence pulse a are established. For example, the optimization factor OFa associated with the pulse sequence pulse a is multiplied with the RF pulses RF1, RF2, RF3, RF4 of the preliminary dynamic pulse Pd in order to obtain the RF pulses RF1a, RF2a, RF3a, RF4a of an optimized dynamic pulse associated with the pulse sequence pulse a. For this purpose, for example, the optimization factor OFa is multiplied with the RF pulse RF1 to obtain RF1a and with the RF pulse RF2 to obtain RF2a, etc.

An optimized dynamic pulse includes, apart from the respective optimized dynamic RF pulses, for example, also the gradient pulses Gx, Gy, Gz of the preliminary dynamic pulse. For example, the optimized dynamic pulse of the pulse sequence pulse a includes the RF pulses RF1a, RF2a, RF3a, RF4a and the gradient pulses Gx, Gy, Gz, the optimized dynamic pulse of the pulse sequence pulse b includes the RF pulses RF1b, . . . and the gradient pulses Gx, Gy, Gz, etc. Finally, the optimized pulse sequence SPo includes the dynamic pulses optimized in this manner. According to the optimized pulse sequence SPo, an imaging of the patient 15 may be carried out by the magnetic resonance apparatus.

Figure 4:
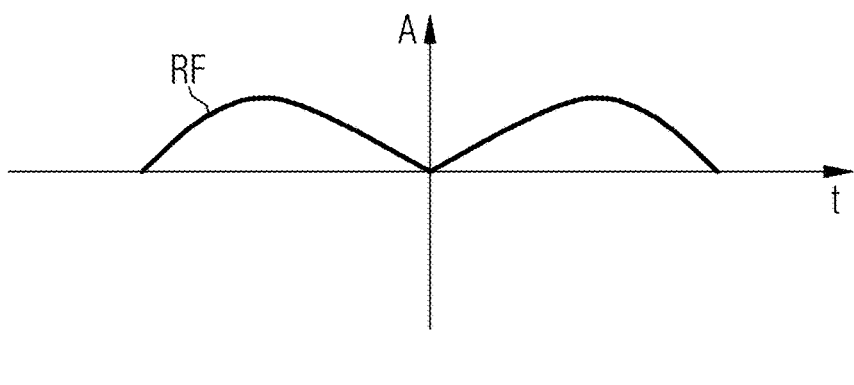
FIG. 4 shows pulse forms of a dynamic pulse according
to a first variant.
Figure 4:
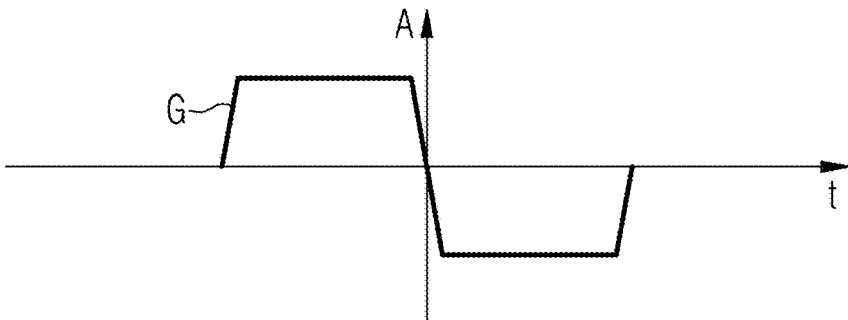
Figure 5:
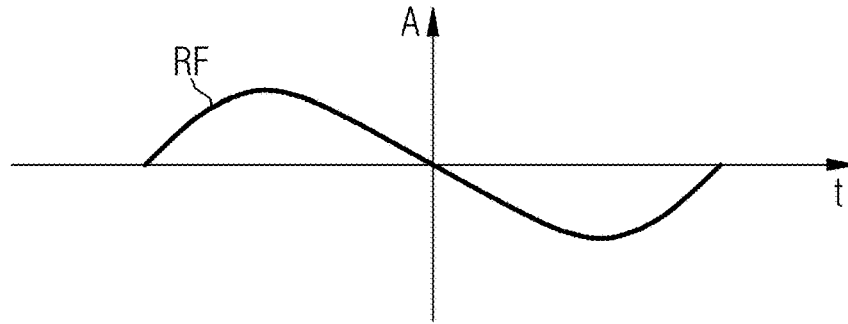
FIG. 5 shows pulse forms of a dynamic pulse according
to a second variant.
Figure 5:
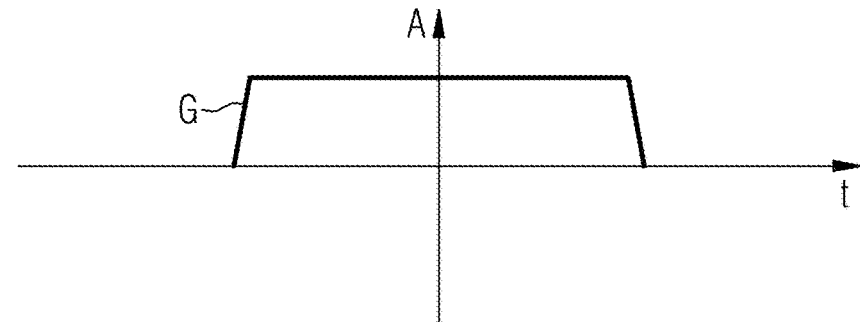

In FIGS. 4 and 5, pulse forms of RF pulses and gradient pulses of a dynamic pulse are represented schematically. In FIG. 4, the RF pulse RF has a symmetrical form, and the gradient pulse G has a temporally antisymmetrical form. In FIG. 4, the RF pulse RF has an antisymmetrical form, and the gradient pulse G has a temporally symmetrical form. In the case of a symmetrical form, the shape of the amplitude A along the time axis t is symmetrical in relation to a symmetry axis. In the case of an antisymmetrical form, the shape of the amplitude A along the time axis t is symmetrical in relation to a symmetry point, but the gradient forms do not have to be constant.

The method described above in detail and the magnetic resonance apparatus disclosed are merely example embodiments that may be modified by a person skilled in the art in a wide variety of ways without departing from the scope of the invention. Further, the use of the indefinite article "a" or "an" does not preclude the possibility that the relevant features may also be present plurally. Similarly, the expression "unit" does not preclude the relevant components consisting of a plurality of cooperating sub-components that may also be spatially distributed, if appropriate.

The elements and features recited in the appended claims may be combined in different ways to produce new claims that likewise fall within the scope of the present invention. Thus, whereas the dependent claims appended below depend from only a single independent or dependent claim, it is to be understood that these dependent claims may, alternatively, be made to depend in the alternative from any preceding or following claim, whether independent or dependent. Such new combinations are to be understood as forming a part of the present specification.

While the present invention has been described above by reference to various embodiments, it should be understood that many changes and modifications can be made to the described embodiments. It is therefore intended that the foregoing description be regarded as illustrative rather than limiting, and that it be understood that all equivalents and/or combinations of embodiments are intended to be included in this description.

The invention claimed is:

1. A method for optimizing a pulse sequence for investigating a patient with a magnetic resonance apparatus, the method being computer-implemented and comprising:

acquiring a B0 map and a B1 map for each of at least one transmission channel of the magnetic resonance apparatus;

establishing a preliminary dynamic pulse based on the at least one B0 map and the at least one B1 map, wherein the preliminary dynamic pulse comprises a preliminary radio frequency (RF) pulse for each of the at least one transmission channel;

establishing at least one optimization map based on the preliminary dynamic pulse, wherein each of the at least one optimization map describes a distribution of an optimization parameter resulting from the preliminary dynamic pulse;

providing an initial pulse sequence; and establishing an optimized pulse sequence based on the initial pulse sequence and the at least one optimization map.

2. The method of claim 1, wherein the at least one optimization map comprises a flip angle map with a flip angle as the at least one optimization parameter.

3. The method of claim 2, wherein the flip angle map is established by a Bloch simulation based on the preliminary dynamic pulse.

4. The method of claim 1, wherein the at least one optimization map comprises a specific absorption rate (SAR) map with a specific absorption rate as the optimization parameter.

5. The method of claim 4, wherein the SAR map is established by provided virtual observation points based on the preliminary dynamic pulse.

6. The method of claim 1, wherein establishing the optimized pulse sequence comprises:

establishing at least one optimization factor based on the at least one optimization map; and establishing an optimized RF pulse for each of the at least one transmission channel based on the at least one optimization factor and the at least one preliminary RF pulse of the preliminary dynamic pulse.

7. The method of claim 6, wherein establishing the at least one optimization factor comprises establishing at least one complex-valued optimization factor based on the at least one optimization map, and wherein establishing the optimized RF pulse comprises establishing the optimized RF pulse via multiplication of the at least one optimization factor with the at least one preliminary RF pulse.

8. The method of claim 6, wherein the initial pulse sequence comprises a plurality of pulse sequence pulses that are temporally sequential, wherein an optimization factor is established for each pulse sequence pulse of the plurality of pulse sequence pulses, wherein for each pulse sequence pulse of the plurality of pulse sequence pulses per transmission channel, an optimized RF pulse is established based on the respective optimization factor and the respective preliminary RF pulse.

9. The method of claim 6, wherein establishing the at least one optimization factor takes place using an EPG model, in accordance with a DiSCoVER method, or using the EPG model, in accordance with a DISCOVER method.

10. The method of claim 6, wherein the establishing of the at least one optimization factor takes place while taking account of a plurality of pulse sequence pulses of the initial pulse sequence.

11. The method of claim 1, wherein establishing the optimized pulse sequence takes place using an EPG model, in accordance with a DiSCoVER method, or using the EPG model, in accordance with a DISCoVER method.

12. The method of claim 1, wherein the establishing of the preliminary dynamic pulse takes place while taking account of at least one first boundary condition, wherein the at least one first boundary condition comprises a maximum SAR burden on the patient caused when the preliminary dynamic pulse is used, a maximum transmission voltage to be applied on the transmission channel when the preliminary dynamic pulse is used, a maximum length of the preliminary dynamic pulse, or any combination thereof.

13. The method of claim 12, wherein the preliminary dynamic pulse also comprises at least one gradient pulse, and wherein the at least one preliminary RF pulse of the preliminary dynamic pulse has a temporally symmetrical form, and the at least one gradient pulse of the preliminary dynamic pulse has a temporally antisymmetrical form.

14. The method of claim 12, wherein the preliminary dynamic pulse also comprises at least one gradient pulse, and wherein the at least one preliminary RF pulse of the preliminary dynamic pulse has a temporally antisymmetrical form, and the at least one gradient pulse of the preliminary dynamic pulse has a temporally symmetrical form.

15. The method of claim 1, wherein the optimized pulse sequence is a pulse sequence according to which at least one spin echo, at least one stimulated echo, or the at least one spin echo and the at least one stimulated echo are generated.

16. The method of claim 1, wherein the respective optimization map includes a plurality of pixels or a plurality of voxels, and assigns a value of the optimization parameter to each pixel of the plurality of pixels or each voxel of the plurality of voxels.

17. A magnetic resonance apparatus comprising:

a system controller configured to optimize a pulse sequence for investigating a patient with the magnetic resonance apparatus, the system controller being configured to optimize the pulse sequence comprising the system controller being configured to:

acquire a B0 map and a B1 map for each of at least one transmission channel of the magnetic resonance apparatus;

establish a preliminary dynamic pulse based on the at least one B0 map and the at least one B1 map, wherein the preliminary dynamic pulse comprises a preliminary radio frequency (RF) pulse for each of the at least one transmission channel;

establish at least one optimization map based on the preliminary dynamic pulse, wherein each of the at least one optimization map describes a distribution of an optimization parameter resulting from the preliminary dynamic pulse;

provide an initial pulse sequence; and establish an optimized pulse sequence based on the initial pulse sequence and the at least one optimization map.

18. In a non-transitory computer-readable storage medium that stores instructions executable by a system controller of a magnetic resonance apparatus to optimize a pulse sequence for investigating a patient with the magnetic resonance apparatus, the instructions comprising:

acquiring a B0 map and a B1 map for each of at least one transmission channel of the magnetic resonance apparatus;

establishing a preliminary dynamic pulse based on the at least one B0 map and the at least one B1 map, wherein the preliminary dynamic pulse comprises a preliminary radio frequency (RF) pulse for each of the at least one transmission channel;

establishing at least one optimization map based on the preliminary dynamic pulse, wherein each of the at least one optimization map describes a distribution of an optimization parameter resulting from the preliminary dynamic pulse;

providing an initial pulse sequence; and establishing an optimized pulse sequence based on the initial pulse sequence and the at least one optimization map.

* * * * *